United States Patent
Plassman

(10) Patent No.: US 8,920,451 B2
(45) Date of Patent: Dec. 30, 2014

(54) DEVICE AND METHOD FOR REMOVING TISSUE INSIDE A BODY VESSEL

(71) Applicant: Cook Medical Technologies LLC

(72) Inventor: Trevor Plassman, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 173 days.

(21) Appl. No.: 13/650,205

(22) Filed: Oct. 12, 2012

(65) Prior Publication Data

US 2014/0107693 A1    Apr. 17, 2014

(51) Int. Cl.
| | | |
|---|---|---|
| *A61B 17/22* | (2006.01) | |
| *A61F 2/01* | (2006.01) | |
| *A61B 17/3207* | (2006.01) | |
| *A61B 17/3201* | (2006.01) | |

(52) U.S. Cl.
CPC .............. *A61F 2/01* (2013.01); *A61B 17/3207* (2013.01); *A61B 17/3201* (2013.01); *A61B 2017/22034* (2013.01)
USPC ........................................................ 606/159

(58) Field of Classification Search
CPC ..... A61B 17/3207; A61B 17/28; A61B 17/29
USPC ......... 606/159, 191, 200, 205–209, 127, 128, 606/114, 170, 172, 179, 180; 604/22; 600/562, 563, 564, 565, 567, 568, 569, 600/570, 571, 572
See application file for complete search history.

(56) References Cited

U.S. PATENT DOCUMENTS

| | | | | |
|---|---|---|---|---|
| 3,749,085 A | * | 7/1973 | Willson et al. | 600/570 |
| 4,020,847 A | * | 5/1977 | Clark, III | 606/159 |
| 4,271,845 A | * | 6/1981 | Chikashige et al. | 600/569 |
| 4,653,496 A | * | 3/1987 | Bundy et al. | 606/159 |
| 4,728,319 A | | 3/1988 | Masch | |
| 4,935,025 A | | 6/1990 | Bundy et al. | |
| 5,007,896 A | * | 4/1991 | Shiber | 604/22 |
| 5,197,482 A | * | 3/1993 | Rank et al. | 600/562 |
| 5,346,497 A | * | 9/1994 | Simon et al. | 606/107 |
| 6,027,460 A | * | 2/2000 | Shturman | 600/585 |
| 6,102,932 A | * | 8/2000 | Kurz | 606/200 |
| 6,818,002 B2 | * | 11/2004 | Shiber | 606/159 |
| 2007/0005084 A1 | | 1/2007 | Clague et al. | |
| 2007/0250096 A1 | * | 10/2007 | Yamane et al. | 606/159 |
| 2012/0109171 A1 | | 5/2012 | Zeroni et al. | |

* cited by examiner

*Primary Examiner* — Tuan V Nguyen
*Assistant Examiner* — George J Ulsh
(74) *Attorney, Agent, or Firm* — Brinks Gilson & Lione

(57) ABSTRACT

Disclosed are a tool and a method for removing tissue inside a body vessel. A first helical coil has a first pitch and a first lumen. The first coil is threaded into a tubular hollow body that is lined with a spiral thread with a second pitch that is substantially the same as the first pitch. The hollow body may be a second coil. A first set of cutting elements extends from the first coil into the first lumen. A second set of cutting elements extends from the hollow body into the first lumen. The first and second sets of cutting elements are arranged with respect to each other such that a screw-like movement of the first helical coil relative to the hollow body causes a cutting element of the first set and a cutting element of the second set to pass each other closely enough to cut tissue.

18 Claims, 5 Drawing Sheets

DEVICE AND METHOD FOR REMOVING TISSUE INSIDE A BODY VESSEL

TECHNICAL FIELD

The present application relates to a device and a method for removing tissue inside a body vessel. More specifically, the application relates to a fibrin removal tool and a method of removing fibrin from a body vessel.

BACKGROUND

When a blood clot forms in a venous vessel and is left in the vessel for more than about two weeks, it starts forming fibrin strands, so-called synechiae. The fibrin strands do not only contribute to an obstruction of the vessel, but also thicken the vessel walls and thus limit the elasticity of the vessel walls.

It is known to reopen a body vessel by implanting a stent that presses the fibrin strands against the vessel wall. It is further known to remove fibrin strands from vessel walls with fairly complex tools.

SUMMARY

According to one aspect of the present invention, a simplified fibrin removal assembly comprises a first helical coil having a first pitch and a first lumen with a first inner diameter, a hollow body having a generally tubular shape, a second lumen lined with a spiral thread forming a second inner diameter, the spiral thread having a second pitch, the second pitch being substantially the same as the first pitch; a first set of cutting elements extending from the first inner diameter inward into the first lumen and configured to cut tissue in a first circumferential direction; and a second set of cutting elements extending from the second inner diameter inward into the first lumen and configured to cut tissue in a second circumferential direction opposite the first circumferential direction, the first and second sets of cutting elements being axially arranged and oriented with respect to each other that a circumferential and axial displacement of the first helical coil relative to the hollow body along the spiral thread causes at least one cutting element of the first set of cutting elements to pass at least one cutting element of the second set of cutting elements closely enough to cut tissue between the cutting element of the first set and the cutting element of the second set. Due to the helical configuration, the assembly can be assembled by a screw-like movement of the first coil and the hollow body relative to each other. A further screw-like movement effects the removal of tissue coated between the cutting element of the first set and the cutting element of the second set.

According to another aspect of the invention, the hollow body and the first helical coil are preferentially made of metal for resilience. For example, the hollow body and the first helical coil may be made of an austenitic alloy, such as an austenitic nickel-chromium-based super alloy. The first coil can be easily manufactured by soldering the first set of cutting elements to the first inner diameter. Likewise, the second set of cutting elements is soldered to the second inner diameter.

According to a further aspect of the invention, the hollow body is a second helical coil. The first and second helical coils may have identical inside diameters to form one lumen.

According to yet another aspect of the invention, each of the cutting elements of the first set may be substantially sickle shaped with a concave edge facing the first circumferential direction. Conversely, the cutting elements of the second set may also be substantially sickle shaped with a concave edge facing the second circumferential direction.

Alternatively, at least the second set of cutting elements may comprise a block-shaped cutting element with a dull edge cooperating with an edge of an associated cutting element of the first set. The cooperating edge of the associated cutting element of the first set may also be a dull edge or an acute edge. Dull edges accomplish cutting by pinching or squeezing, while acute edges may cut into the tissue. With both types of edges present, the fibrin removal tool may cut the fibrin strands by pinching or cutting or by a combination of both.

In another embodiment of the invention, at least the cutting elements of the first set have a shark fin shape with a straight cutting edge. The associated cutting elements of the second set may also have a shark fin shape with a straight cutting edge.

According to another aspect of the invention, the fibrin removal assembly further comprises an elongated tube connected to a proximal end of the hollow body and an elongated wire extending through the tube and connected to a proximal end of the first helical coil, the elongated tube and the elongated wire being configured to perform a relative circumferential movement in with respect to each other. This arrangement allows an operator to cause the screw-like movement between the first coil and the hollow body from a remote place outside the body vessel.

Additionally, the fibrin removal assembly may comprise an outer catheter configured to surround at least a distal portion of the elongated tube and the elongated wire, the elongated wire and the elongated tube each having a greater length than the outer catheter. The outer catheter facilitates insertion into the body vessel so that the fibrin removal device can be positioned proximate the tissue to be removed.

According to a further aspect of the invention, a method of removing tissue inside a body vessel comprises the steps of: distally inserting an outer catheter into a body vessel; positioning a distal end of the outer catheter proximate a location of tissue to be removed; distally inserting a fibrin removal tool into the outer catheter, the fibrin removal tool having a first helical coil with a first pitch and with a first lumen having a first inner diameter, a hollow body having a generally tubular shape, a second lumen with a second inner diameter, and a spiral thread lining the lumen with a second pitch, the second pitch being substantially the same as the first pitch, a first set of cutting elements extending from the first inner diameter inward into the first lumen and configured to cut tissue in a first circumferential direction, and a second set of cutting elements extending from the second inner diameter inward into the first lumen and configured to cut tissue in a second circumferential direction opposite the first circumferential direction, the first and second sets of cutting elements being axially arranged and oriented with respect to each other that a circumferential and axial displacement of the first helical coil relative to the hollow body along the spiral thread causes at least one cutting element of the first set of cutting elements to pass at least one cutting element of the second set of cutting elements closely enough to cut tissue between the cutting element of the first set and the cutting element of the second set; positioning the fibrin removal tool proximate the distal end of the outer catheter; causing a spiral-like relative movement between the first helical coil and the hollow body so as to cut the tissue located between the at least one cutting element of the first set and the at least one cutting element of the second set; and distally removing the fibrin removal tool.

Because the cutting elements are located on the inside of the removal tool, any risk of injury to the surrounding body vessel wall is reduced. The removed tissue is inside the first lumen and is thus transported out of the body vessel by removing the fibrin removal tool.

DETAILED DESCRIPTION OF THE DRAWINGS

When a blood clot forms in a venous vessel and is left in the vessel for more than about two weeks, it starts forming fibrin strands, so-called synechiae. The fibrin strands do not only contribute to an obstruction of the vessel, but also thicken the vessel walls and thus limit the elasticity of the vessel walls. Thus, the present invention provides a safe way of reopening the vessel by removing fibrin strands while reducing the risk of injury to the vessel walls.

Figure 1:
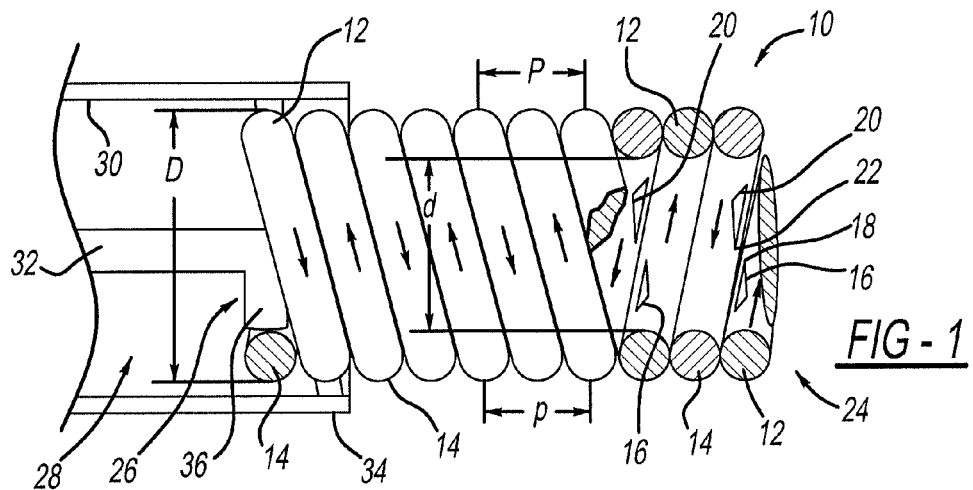
FIG. 1 shows a partially cut-away view of a fibrin removal tool according to a first aspect of the invention.

Now referring to FIG. 1, a fibrin removal tool 10 comprises a first helical coil 12 and a second helical coil 14. The two helical coils 12 and 14 are wound in the same orientation and have generally identical axial distances P between the axial centers of their windings. This axial distance P is commonly called the pitch of coils 12 and 14. The two coils 12 and 14 are intertwined with each other so that, at least along at least an axial portion, windings of the first helical coil 12 alternate with windings of the second helical coil 14. In FIG. 1, each of the two coils 12 and 14 is formed from wire of the same thickness as the other, and the coils 12 and 14 have the same diameter. The arrangement of FIG. 1, however, would also work with coils differing in diameter or wire thickness or both.

Preferably, each of the coils 12 and 14 has a relaxed shape that provides a sufficient gap between individual windings that a respective winding of the other coil fits in the gap and that the two coils 12 and 14 are easily movable relative to each other in a screw-like movement. The term "relaxed state" in this context means a shape that the coil adopts without the influence of external forces. Further, in this context, a screw-like movement is a rotation about an axis with a superimposed axial movement proportional to the degrees of rotation. The amount of the superimposed axial movement is determined by the pitch P of the coils 12 and 14.

The first helical coil 12 has a first set of cutting elements 16 attached to the inside of the coil windings and extending inward from the inner diameter d into the lumen of the first helical coil 12. The cutting elements 16 are arranged in a way that at least one generally radially extending edge 18 is axially arranged close to the adjacent winding of the second helical coil 14. The second helical coil 14 has a second set of cutting elements 20 attached to the inside of the coil windings and extending inward from the inner diameter d into the lumen of the second helical coil 14. The cutting elements 20 are arranged in a way that at least one generally radially extending edge 22 is axially arranged close to the adjacent winding of the second helical coil 14. Furthermore, the edges 18 have a circumferential orientation opposite to the edges 22. The expression "generally radial" means that these edges have at least one portion that extends radially inward to such a degree that it can exert a circumferential grip on fibrin.

A screw-like movement of the two coils 12 and 14 relative to each other, in which the edges 18 and 22 approach each other leads to a cut of fibrin strands located between pairs of cutting elements 18 and 22 in a scissor-like manner.

An optimum of space between the windings of the two coils 12 and 14 can be experimentally determined. On one hand, the coils 12 and 14 are preferably easily movable relative to each other. On the other hand, the slack between the coils should be small enough to allow for effective severance of fibrin strands. Accordingly, the coils 12 and 14 preferably have a stiffness that allows the screw-like relative movement by rotating the proximal ends of the coils 12 and 14 without excessive deformation. A limited torsional deformation that leaves the cutting function operational is not excessive.

For cutting the fibrin strands, the edges 18 and 22 may form acute angles as indicated in FIG. 1. But, as known from generally available scissors or shears, sharp edges are not crucial as long as the cutting elements 18 and 22 slide past each other at a distance small enough to sever the fibrin strands. Thus, the term "cutting" is to be understood in a broad sense and includes squeezing or pinching that leads to a severance of fibrin strands. A large variety of shapes is suited for forming the cutting elements. Such shapes will be discussed in more detail in connection with FIGS. 2 through 5.

The two coils 12 and 14 have distal ends 24 that may be flattened or rounded for insertion into a venous vessel. The proximal ends 26 of the coils 12 and 14 are fastened to an actuation arrangement 28 for remotely causing the screw-like movement between the coils 12 and 14 as indicated by small arrows on the windings of the respective coils 12 and 14. The actuation arrangement 28 comprises a tube 30 with a distal end 34 attached to the outside of the proximal end 26 of coil 12 and a wire 32 with a distal end 36 attached to the inside of coil 14 at the proximal end 26. The tube 30 has a lumen with a diameter larger than the outer diameter D of at least the second coil 14 near the proximal end 26. Where, as here, the coils 12 and 14 have a generally identical outer diameters D (within manufacturing tolerances), the lumen of the tube has a diameter larger than the outer diameter D of both coils 12 and 14 in the area of the proximal end 26. The wire 32 extends through the tube 30 to a proximal handle or the like for rotating the wire 32. Likewise, the tube 30 may be connected to a proximal device for rotating the tube 30 opposite to the wire 32. For the above-described function of the fibrin removal tool 10, a rotation of either the first coil 12 or the second 14 is sufficient for causing the screw-like relative movement.

Figure 2:
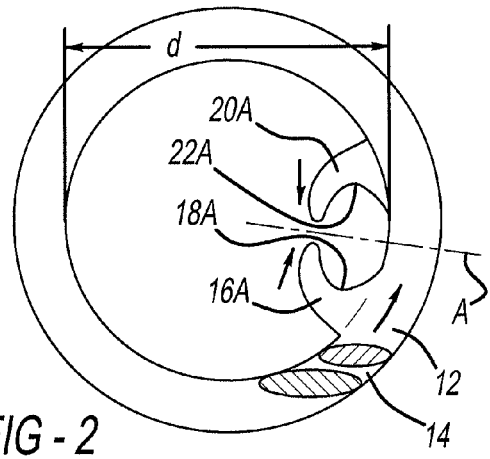
FIG. 2 shows a first radial profile variation of cutting elements in the fibrin cutter of FIG. 1.

Now referring to FIG. 2, the first coil 12 and the second coil 14 are schematically shown with a first cutting element 16A protruding radially inward from the inner diameter d of the first coil 12 into the lumen of coil 12. A second cutting element 20A protrudes radially inward from the inner diameter d of the second coil 14 into the lumen of coil 14. In the embodiment of FIG. 2, the two cutting elements are of about identical shape. The cutting element 20 is arranged in a position rotated by 180 degrees relative to the cutting element 16A about a radial axis A. Each cutting element 16A and 20A has a sickle-like or crescent shape, where the edges 18A and 22A form concave sickle blades facing each other.

The radially inward ends of the sickle-like cutting elements 16A and 20A are bent toward each other so as to retain any material located between the ends and the coil windings. As the screw-like movement of the two coils relative to each other moves the cutting elements 16A and 20A toward each other as indicated by arrows, any material located between the two cutting elements 16A and 20A is thus retained between the cutting elements. If the edges 18A and 22A are sharpened, a cut into the retained material may occur as soon as the edges 18A and 22A exert a certain pressure on the retained material. Otherwise, the retained material will be severed as the edges 18A and 22A pinch the retained material and possibly make contact with each other.

Figure 3:
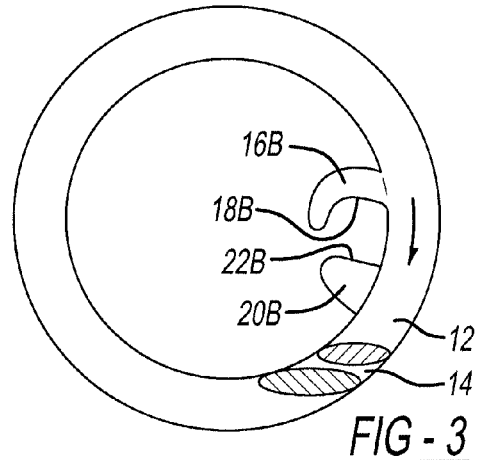
FIG. 3 shows a second radial profile of cutting elements in the fibrin cutter of FIG. 1.
Figure 4:
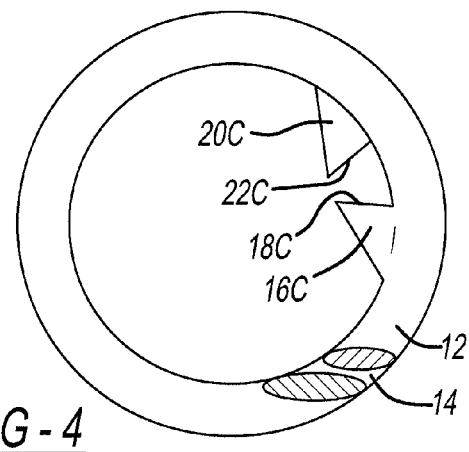
FIG. 4 shows a third radial profile variation of cutting elements in the fibrin cutter of FIG. 1.
Figure 5:
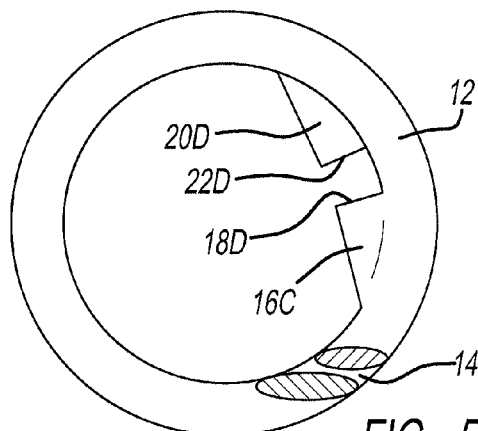
FIG. 5 shows a fourth radial profile variation of cutting elements in the fibrin cutter of FIG. 1.

It is evident from FIG. 2 and the further embodiments of FIGS. 3 through 5 that the severance of material occurs inside the lumen of the two coils 12 and 14. Compared to devices, in which the fibrin strands are severed between two cylindrical walls, the material severed inside the lumen of the coils can be easily removed from the vessel without requiring additional milled channels along any cylindrical walls.

As FIG. 3 illustrates, the direction of the relative screw-like movement of the two coils 12 and 14 can be reversed where the coil 12 carries a cutting element 16B with a generally radial edge 18B facing in the clockwise circumferential direction. In the embodiment shown in FIG. 3, the cutting element 16B has a sickle-like shape similar to the cutting elements 16A and 20A of FIG. 2.

Notably, however, coil 14 carries a cutting element 20B that is rather block-shaped. While it has an edge 22B facing edge 18B, the edge 22B may be dull and not suited to cut any fibrin strands by itself. Thus, the cutting element 20B operates as a retaining block that prevents fibrin strands from moving in the clockwise direction as the cutting element 16B approaches the cutting element 20A. Only the interaction between the two edges 18B and 22B causes a severance of strands. To this end, the cutting element 16B again is bent toward the cutting element 18B so as to restrict a radially inward movement of fibrin strands located between the two cutting elements 16B and 20B as the two cutting elements 16B and 20B approach each other. With further relative movement of the two cutting elements, the fibrin strands are then severed, because the two cutting elements 18B and 22B squeeze the strands into separation, or because the edge 18B of cutting element 16B acts like a blade, or a due to a combination of both.

Now referring to FIG. 4, two cutting elements 16C and 20C each have a shape resembling a shark fin. Each one of the two cutting elements 16C and 20C is shaped like a triangle with two acute angles and one obtuse angle. The obtuse angles are located in the corners that are formed by the edges 18C and 22C on one side and the coils 12 and 14 on the other side, respectively. Thus the edges 18C and 22C facing each other and extending in the generally radially inward direction have a smaller distance to each other at their radially inward tips than in locations radially closer to their attachment to the coils 12 and 14, respectively. Like the previously described sickle shape, these angular dimensions enhance the retention of fibrin strands between the two cutting elements.

FIG. 5 shows a variation of the configuration of FIG. 4, in which two cutting elements 16D and 20D have generally radial edges 18D and 22D that are straight. The embodiment of FIG. 5 illustrates that the edges 18D and 22D may extend radially or may form a very small angle between each other. Preferably, however, the straight edges 18D and 22D have no greater distance from each other at their radially inward tips than in locations closer to the windings of the coils 12 and 14.

FIGS. 6 through 9 depict several variations in the shapes of cutting elements in circumferential cross-sections, i.e. views in a radially outward direction from the center of coils 12 and 14.

Figure 6:
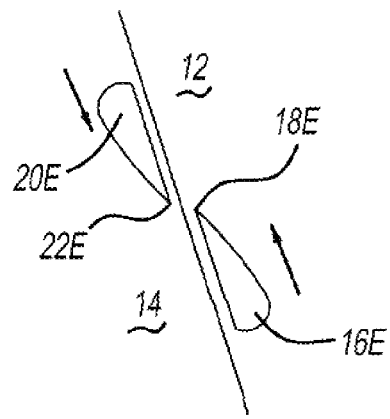
FIG. 6 shows a first axial profile variation of cutting elements in the fibrin cutter of FIG. 1.

In FIG. 6, for example, two cutting elements 16E and 20E each have an edge 18E and 22E, respectively, that faces the respective edge of the other cutting element. In the embodiment of FIG. 6, both edges 18E and 22 E form an acute angle to give them the capability of cutting fibrin strands. Cross-sections similar to those of the edges 18E and 22E of cutting elements 16E and 20E may, for example, be adopted by the embodiments of FIGS. 2, 4, and 5. Contours of the cutting elements 16E and 20E remote from the edges 18E and 22E are of lesser importance. But it is preferred that the cutting elements have a convex shape in circumferential cross-sections intersecting the edges 18E and 22E to reduce the likelihood of entangling fibers on portions of the cutting elements that have no cutting function.

Figure 7:
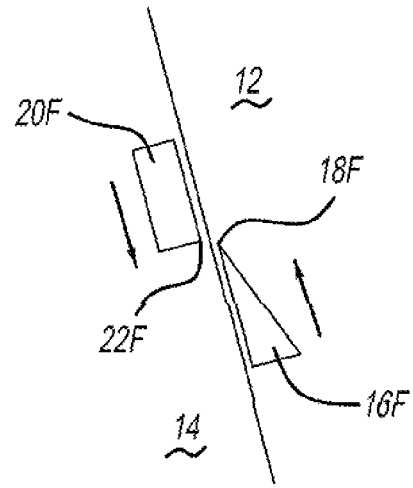
FIG. 7 shows a second axial profile variation of cutting elements in the fibrin cutter of FIG. 1.

FIG. 7 shows an example of a pair of cutting elements 16F and 20F with shapes differing from one another. While cutting element 16F has an edge 18F with an acute angle similar to cutting elements 16E and 20E of FIG. 6, cutting element 20F forms a retaining block with an edge 22F that is dull. Dull in this context means that an edge is not suited to perform a blade function of its own. Here, the dull edge 22F forms an angle of about 90 degrees. When the two cutting elements 16F and 20F approach each other, fibrin stands located between the two cutting elements 16F and 20 may be cut by cutting element 16F or squeezed into separation by the shrinking distance between edges 18F and 22F, or by both of these processes. The profiles shown in FIG. 7 may, for instance, be adopted for an arrangement as shown in FIG. 3.

Figure 8:
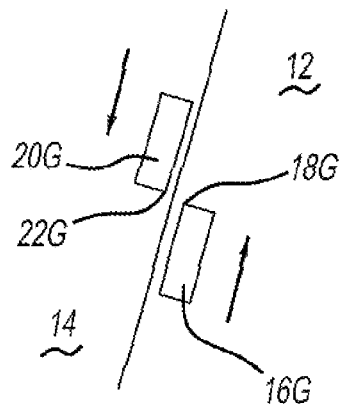
FIG. 8 shows a third axial profile variation of cutting elements in the fibrin cutter of FIG. 1.
Figure 9:
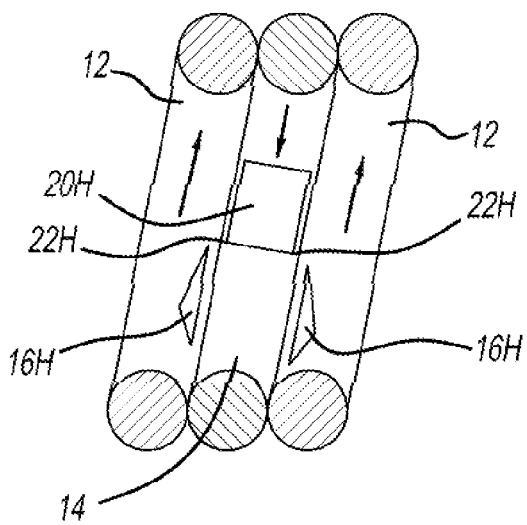
FIG. 9 shows a fourth axial profile variation of cutting elements in the fibrin cutter of FIG. 1.

FIGS. 8 and 9 illustrate that various shapes may be adopted for the cutting elements 16G, 20G, 16H, and 20H. In FIG. 8, both edges 18G and 22G of cutting elements 16G and 20G are dull and effect a severance of fibrin stands by squeezing or pinching the strands into separation. FIG. 9 illustrates how one cutting element 20H may have two edges 22H that each may cooperate with a different cutting element 16H on opposite axial sides of the cutting element 20H.

Figure 10:
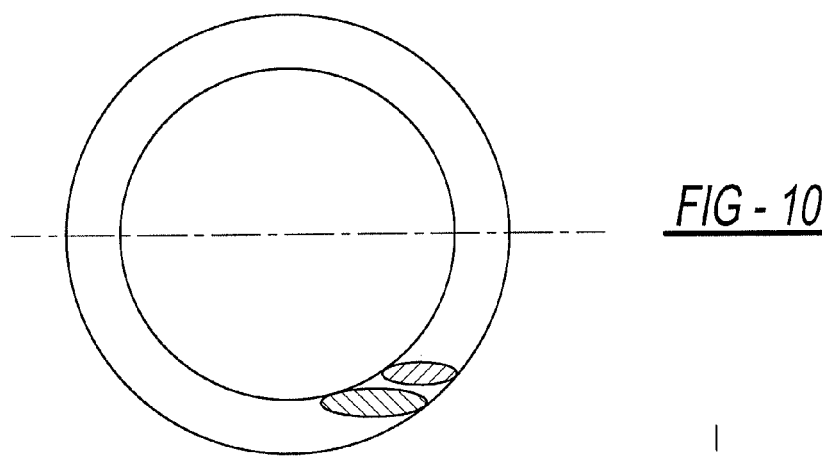
FIG. 10 shows a first circumferential distribution of cutting elements in the fibrin cutter of FIG. 1.
Figure 11:
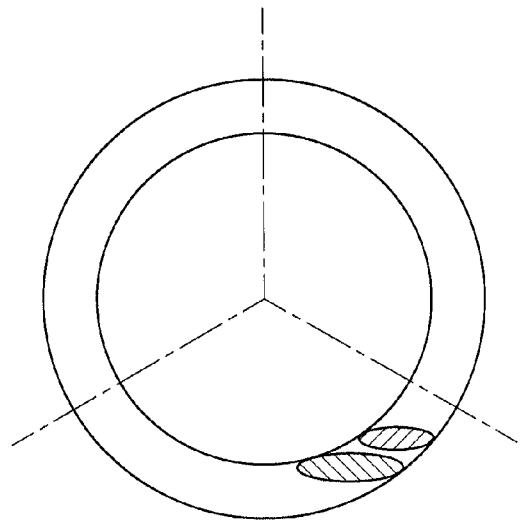
FIG. 11 shows a second circumferential distribution of cutting elements in the fibrin cutter of FIG. 1.
Figure 12:
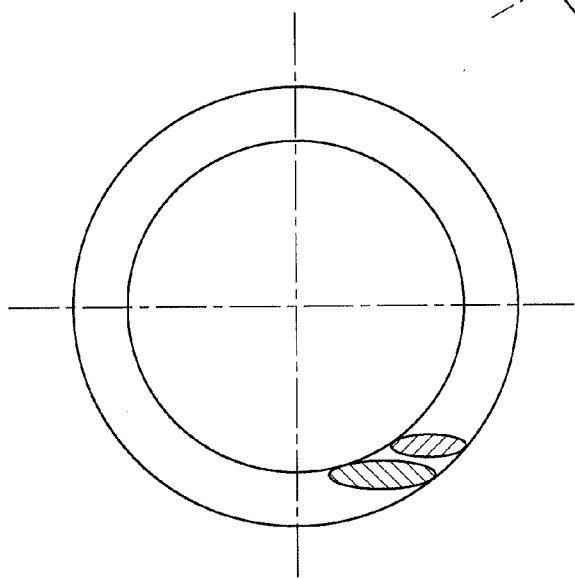
FIG. 12 shows a third circumferential distribution of cutting elements in the fibrin cutter of FIG. 1.

Further, FIGS. 10 through 12 indicate that the circumferential arrangement of the cutting elements is not limited to one angular position. Cutting elements may be arranged offset by 180 degrees as indicated in FIG. 10 by a broken line. FIGS. 11 and 12, respectively, indicate angular locations offset by 120 degrees and 90 degrees, respectively. It is evident that a random distribution along the circumferential direction is well within the scope of the present invention. Additionally, several cutting elements may distributed along the circumference of one coil winding, especially near the proximal end of the coils 12 and 14.

Figure 13:
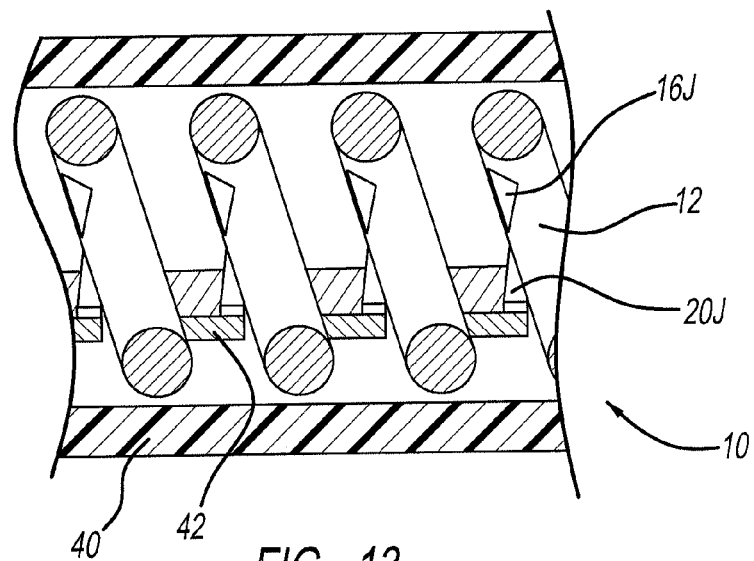
FIG. 13 shows an alternative embodiment of a fibrin cutter according to a further aspect of the invention.

FIG. 13 an alternative fibrin removal tool that comprises only one helical coil 12. Instead of a second helical coil, a flexible coaxial tubular member or sheath 40 surrounds the coil 12. The coil 12 carries cutting elements 16J that may be shaped like any of the previously described cutting elements of FIGS. 2 through 9. The sheath 40 has guide blocks 42 attached to its inside lumen that protrude radially inward between the windings of coil 12. Cutting elements 20J are mounted on the guide blocks 42 to protrude into the lumen of coil 12 and to cooperate with cutting elements 16J of coil 12. Cutting elements 20J may also have any shape described in the previous figures.

The guide blocks 42 guide the coil 12 during the screw-like relative movement between the coil 12 and the sheath 40 and thus form a thread on the inside wall of the sheath 40 cooperating with the windings of coil 12. In order to form the thread, the guide blocks 42 may be formed by one continuous helical guide block or, as shown, comprise several separate guide blocks 42. The amount of axial displacement of the coil 12 relative to the sheath 40 is determined by the pitch of the guide blocks 42.

Thus, FIG. 13 shows that the invention is not limited to two intertwined coils if the arrangement allows to cut fibrin strands inside the interior lumen of the two elements that perform the screw-like movement relative to each other.

The screw-like movement allows for easy assembly of the first coil 12 and the sheath 40 or the second coil 14 by screwing them into each other. With a purely circumferential movement between the two parts 12 and 14 or 12 and 40, respectively, cutting elements protruding into the inner lumen from the outside would be in the way of an axial insertion of one of the two parts into the other and thus complicate the assembly. Accordingly, the screw-like movement allows for the cutting elements on both the first coil and the sheath 40 or the second coil 14, respectively, to protrude into the inner lumen of the first coil 12 without interfering with the assembly of the fibrin removal tool 10.

The various embodiments of fibrin removal tools described may, for example, be manufactured by soldering the cutting elements onto the inside of the associated coil or sheath. The outside of the respective coil or sheath remains smooth so that the vessel wall is guarded form the cutting elements.

Figure 14:
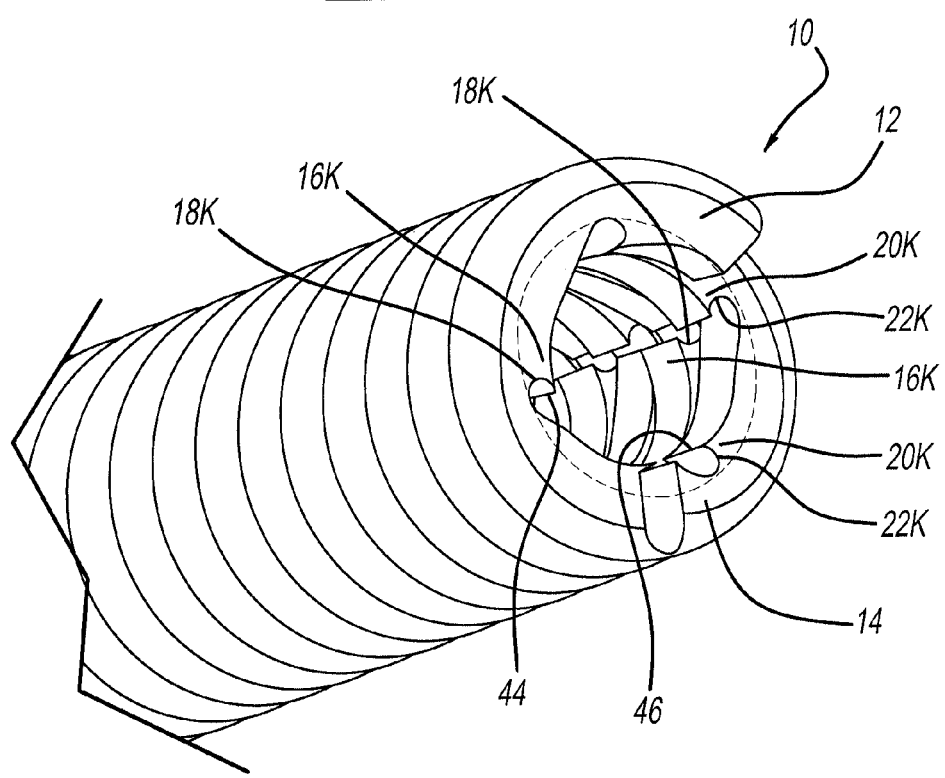
FIG. 14 shows a further alternative embodiment of a fibrin cutter according to yet another aspect of the invention.

Now referring to FIG. 14, in another embodiment of the invention, the two coils 12 and 14 carry cutting elements 16K and 20K that perform a dual function. In the embodiment shown, the cutting elements 16K and 20K are formed unitarily with the respective coils 12 and 14. This can be accomplished, for example, by removing material on the inside of the coils 12 and 14 in specific locations. Initially, the coils have a smaller inner diameter than the final inner diameter d, which is indicated by a broken line. A milling tool is axially inserted into each of the coils 12 and 14 before assembly to produce circumferential undercuts. For example, in the embodiment shown, each coil has axially extending grooves that are arranged at an oblique angle relative to a radial direction. While the embodiment shows cutting elements unitary with the coils 12 and 14, the cutting elements 18K and 22K may also be attached to the inside of the coils as described in connection with the previous embodiments.

Each cutting element 16K and 20K forms a wedge protruding from the inner diameter d with an axially extending blade 44 and 46, respectively. The blades 44 of the cutting elements 16K on coil 12 face in one circumferential direction, and the blades 46 of the cutting elements 20K face in the opposite circumferential direction. In the example shown, the blades 44 are oriented to cut tissue in the counterclockwise direction, and the blades 46 are oriented to cut tissue in the clockwise direction.

Additionally, the generally radially extending edges 18K and 22K of the grooves form pairs of cooperating edges that pinch tissue caught between them when the coils 12 and 14 are rotated relative to each other in the cutting directions of the axial blades 44 and 46. This function is similar to that of the embodiment of FIG. 8. This movement of the cutting elements 16K and 20K causes the blades 44 and 46 to circumferentially penetrate and sever tissue with axially extending cuts. As the edges 18K and 22K approach each other, they sever further tissue caught between them by pinching.

Suitable materials for the two coils or for the coil and the sheath, respectively, and for the cutting elements of all embodiments include stainless steel and austenic nickel-chromium-based super alloys, such as Inconel. The outside dimensions of the fibrin removal tool 10 can be adapted to the diameter of the body vessel, into which the fibrin removal tool 10 is to be inserted. This allows cutting of fibrin strands close to the vessel wall and without the prior insertion of an implant protecting the vessel walls. The two coils or the coil and the sheath, respectively, can then be coaxially connected by being screwed into each other until the cutting elements are properly aligned for cutting.

To reduce adherence of the outside of the fibrin removal device to the vessel walls and to the tissue, coatings may be applied before assembly. One suitable coating is, for example, PTFE.

Figure 15:
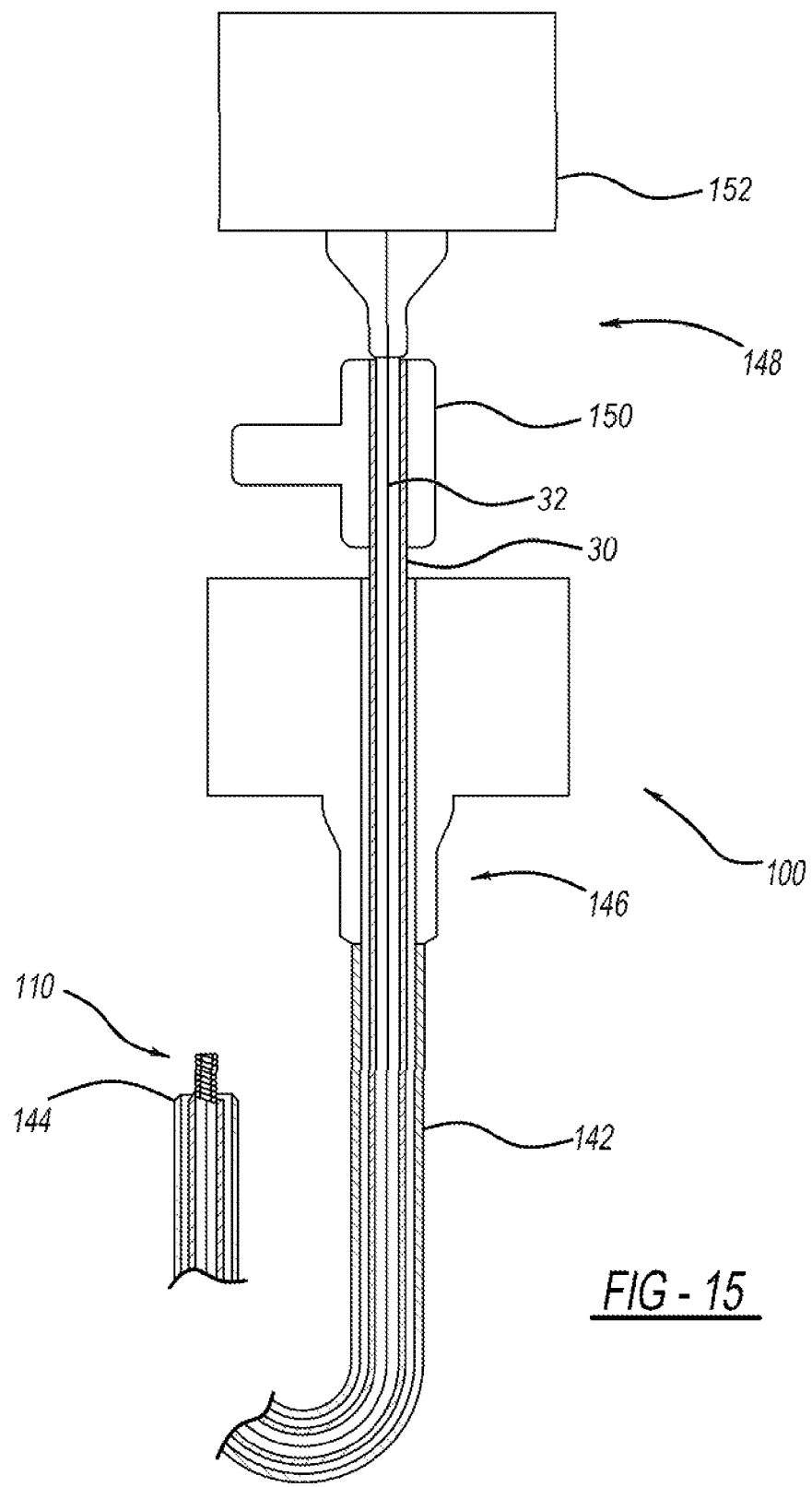
FIG. 15 shows a surgical catheter tool for removing fibrin according to another aspect of the invention.

FIG. 15 shows an example of a fibrin removal assembly 100 with a fibrin removal tool 110 that may be configured according to any one of the preceding figures or a modification thereof.

The fibrin removal assembly 100 has an outer sheath or catheter 142 that is initially inserted into a body vessel in a known manner, for example along a guide wire. Inside the outer catheter 142, the fibrin removal tool 110 extends from the distal end 144 of the outer catheter 142 through the lumen of the outer catheter 142 past the proximal end 146 of the outer catheter to an actuation system 148 of the fibrin removal tool 110.

At the distal end 144, the parts carrying the cutting elements extend beyond the outer catheter 142. As shown in FIG. 1, one of the parts is connected to the tube 30, and the other one to wire 32. The tube 30 and the wire 32 extend coaxially through the outer catheter 142 to the actuation system 148.

The actuation system 148 comprises a first handle or positioning device 150 attached to the tube 30. The wire 32 extends through the positioning device 150 to a rotating device 152. The rotating device 152 is configured to rotate the wire 32 inside the tube 30 to cause a relative screw-like movement between the tube 30 and the wire 32. The positioning device 150 may also be capable of rotating the tube 30 relative to the outer catheter 142 and relative to the wire 32. As shown in FIG. 1 on the example of the two coils 12 and 14, a relative rotation between the tube 30 and the wire 32 causes the screw-like movement between the first and second coils 12 and 14. For devices in which the tube 30 is attached to or unitarily formed with sheath 40 of FIG. 13, the resulting effect is the same.

The relative movement between the tube 30 and the wire 32 is selected to occur in directions that cause the edges of each pair of associated cutting elements to approach each other so as to sever any fibrin strands caught between the generally radial edges.

While the foregoing description made reference to fibrin strands and cutting thereof, the invention is not limited to such a use and is suited for taking biopsy samples or for any cutting of intravascular tissue with a reduced risk of damaging the vessel wall.

The foregoing description of various embodiments of the invention has been presented for purposes of illustration and description. It is not intended to be exhaustive or to limit the invention to the precise embodiments disclosed. Numerous modifications or variations are possible in light of the above teachings, and the properties of one embodiment may be modified with properties of another. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A fibrin removal assembly comprising
a first helical coil having a first pitch and a first lumen with a first inner diameter,
a hollow body having a generally tubular shape, a second lumen lined with a spiral thread forming a second inner diameter, the spiral thread having a second pitch, the second pitch being substantially the same as the first pitch,
a first set of cutting elements including a first plurality of cutting elements extending from the first inner diameter inward into the first lumen and configured to cut tissue in a first circumferential direction, and
a second set of cutting elements including a second plurality of cutting elements extending from the second inner diameter inward into the first lumen and configured to cut tissue in a second circumferential direction opposite the first circumferential direction, the first and second sets of cutting elements being axially arranged and oriented with respect to each other that a circumferential and axial displacement of the first helical coil relative to the hollow body along the spiral thread causes an edge of each of the cutting elements of the first plurality of cutting elements to pass an edge of one of the cutting elements of the second plurality of cutting elements closely enough to cut tissue between the first plurality of cutting elements and the second plurality of cutting elements.

2. The fibrin removal assembly of claim 1, wherein the hollow body and the first helical coil are made of metal.

3. The fibrin removal assembly of claim 2, wherein the hollow body and the first helical coil are made of an austenitic alloy.

4. The fibrin removal assembly of claim 3, wherein the hollow body and the first helical coil are made of an austenitic nickel-chromium-based super alloy.

5. The fibrin removal assembly of claim 2, wherein the first set of cutting elements is soldered to the first inner diameter.

6. The fibrin removal assembly of claim 2, wherein the second set of cutting elements is soldered to the second inner diameter.

7. The fibrin removal assembly of claim 1, wherein the hollow body is a second helical coil.

8. The fibrin removal assembly of claim 1, wherein the first inner diameter is equal to the second inner diameter.

9. The fibrin removal assembly of claim 1, wherein each of the cutting elements of the first set is substantially sickle shaped with a concave edge facing the first circumferential direction.

10. The fibrin removal assembly of claim 9, wherein the cutting elements of the second set are substantially sickle shaped with a concave edge facing the second circumferential direction.

11. The fibrin removal assembly of claim 1, wherein at least the second set of cutting elements comprises a cutting element with a dull edge cooperating with an edge of an associated cutting element of the first set.

12. The fibrin removal assembly of claim 11, wherein the cooperating edge of the associated cutting element of the first set is a dull edge.

13. The fibrin removal assembly of claim 1, wherein at least the cutting elements of the first set have a shark fin shape with a straight cutting edge.

14. The fibrin removal assembly of claim 13, wherein the cutting elements of the second set also have a shark fin shape with a straight cutting edge.

15. The fibrin removal assembly of claim 1, wherein each of the cutting elements of the first set further comprises an axially extending blade facing in the first circumferential direction.

16. The fibrin removal assembly of claim 15, wherein each of the cutting elements of the second set further comprises an axially extending blade facing in the second circumferential direction.

17. The fibrin removal assembly of claim 1, further comprising an elongated tube connected to a proximal end of the hollow body and an elongated wire extending through the tube and connected to a proximal end of the first helical coil, the elongated tube and the elongated wire being configured to perform a relative circumferential movement in with respect to each other.

18. The fibrin removal assembly of claim 17, further comprising an outer catheter configured to surround at least a distal portion of the elongated tube and the elongated wire, the elongated wire and the elongated tube each having a greater length than the outer catheter.

* * * * *